United States Patent [19]

Fogarty et al.

[11] Patent Number: 4,483,340
[45] Date of Patent: Nov. 20, 1984

[54] DILATATION CATHETER

[75] Inventors: Thomas J. Fogarty, 770 Welch Rd., Palo Alto, Calif. 94304; Thomas B. Kinney, Mountain View, Calif.

[73] Assignee: Thomas J. Fogarty, Palo Alto, Calif.

[21] Appl. No.: 198,529

[22] Filed: Oct. 20, 1980

[51] Int. Cl.³ .................................. A61M 29/02
[52] U.S. Cl. ................................ 128/344; 128/348.1
[58] Field of Search ............ 128/344, 349 B, 349 BV, 128/325, DIG. 9, 348.1; 604/96–103

[56] References Cited

U.S. PATENT DOCUMENTS

| | | | |
|---|---|---|---|
| 2,616,429 | 11/1952 | Merenlender | 128/350 |
| 2,688,329 | 9/1954 | Wallace | 128/349 |
| 3,426,744 | 2/1969 | Ball | 128/1 |
| 3,799,172 | 3/1974 | Szpur | 128/349 R |
| 3,837,347 | 9/1974 | Tower | 128/404 |
| 3,996,938 | 12/1976 | Clark | 128/348 |
| 4,046,151 | 9/1977 | Rose | 128/404 |
| 4,105,022 | 8/1978 | Antoshkiw et al. | 128/349 B X |
| 4,261,339 | 4/1981 | Hanson et al. | 128/348 X |
| 4,292,974 | 10/1981 | Fogarty et al. | 128/344 |

FOREIGN PATENT DOCUMENTS 512456  9/1939  United Kingdom ............... 128/344

*Primary Examiner*—Michael H. Thaler
*Attorney, Agent, or Firm*—Limbach, Limbach & Sutton

[57] ABSTRACT

A dilatation catheter of the type having a balloon element adapted to be retracted by axial twisting following deflation is provided with a pair of concentrically related balloon twisting elements, one of which is adapted to be removed following full wind up of the balloon element so that the relative stiffness of the twisted balloon section of the catheter will be approximately the same as that of the balance of the catheter.

7 Claims, 4 Drawing Figures

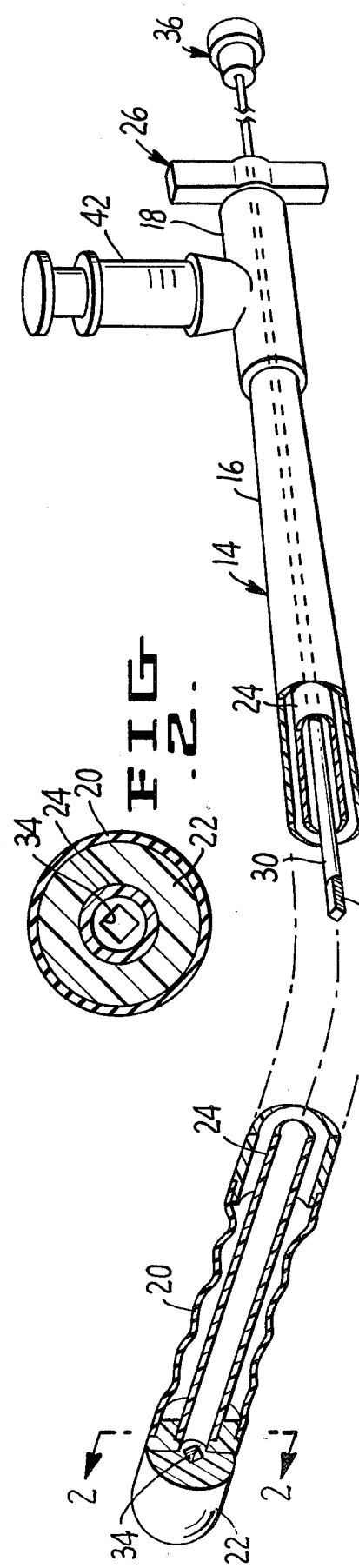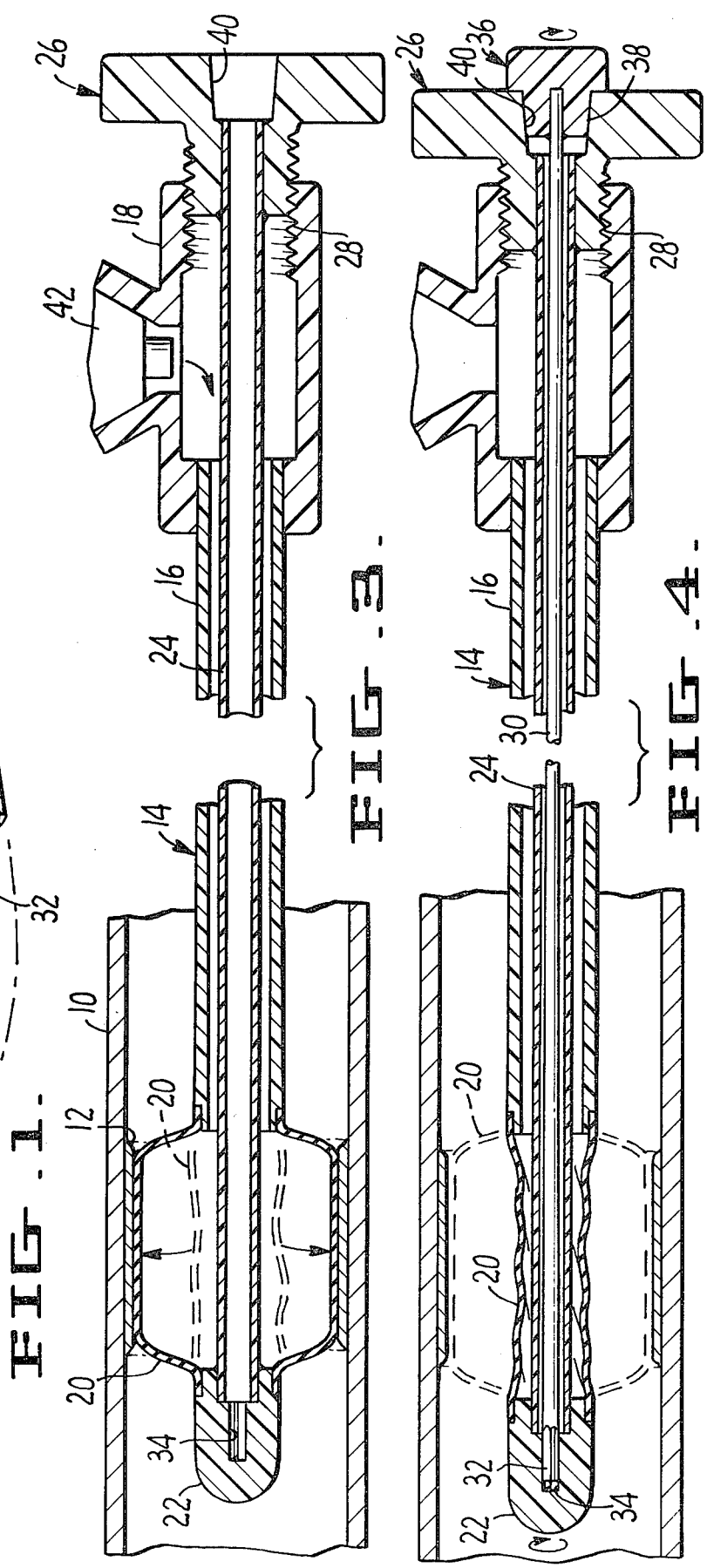

DILATATION CATHETER

RELATED APPLICATION

The subject dilatation catheter is an improvement upon the dilatation catheter of commonly owned, copending application Ser. No. 116,816, filed Jan. 30, 1980, now U.S. Pat. No. 4,292,974, by Thomas J. Fogarty and Albert K. Chin for DILATATION CATHETER APPARATUS AND METHOD.

BACKGROUND OF THE INVENTION

This invention relates to a catheter for use in dilating occluded blood vessels and more particularly to a catheter whereby dilatation is achieved by means of a balloon element of relatively large diameter. The balloon element is inflated to compress the occlusion. After subsequent deflation the balloon element has its transverse dimension reduced to a minimal size to enable proper placement of the catheter within the lumen of an occluded artery or vein.

SUMMARY OF THE INVENTION

The balloon element of the catheter of the above-identified patent application is reduced in transverse dimension by axial twisting by means of an axially disposed non-removable wire. The wire was sufficiently strong to apply the degree of torque necessary to initiate the twisting of the balloon. However, once the balloon had been twisted to decrease the diameter of the balloon element to minimal size the balloon section of the catheter tended to be more rigid, due to the composite factors of balloon twisting and core wire presence, than the rest of the catheter. This tended to limit the adaptability of the catheter to change its shape in conformance with the shape of the blood vessel through which it was being threaded.

In the present catheter this problem has been overcome by providing the catheter with a pair of concentrically disposed balloon twisting elements. Both of the twisting elements are maintained in place while the balloon is being twisted. After the balloon has been twisted, one of the twisting elements is removed to thereby decrease the stiffness of the twisted balloon section of the catheter so that the balloon section has a flexibility comparable to that of the rest of the catheter.

The principal object of the invention is to provide a twist-type dilatation catheter with a multiple component balloon twister, with part of the twister being removable to enhance the flexibility of the twisted balloon section of the catheter.

Other objects and advantages of the invention will be apparent from the following description taken in conjunction with the drawing forming part of this specification.

DESCRIPTION OF THE DRAWING

FIG. 1 is a view in perspective, partly in elevation and partly broken away, of the catheter of the invention.

FIG. 2 is an enlarged view taken along lines 2—2 of FIG. 1.

FIG. 3 is a view in diametral section of the catheter in place within a blood vessel in inflated condition.

FIG. 4 is a view similar to that of FIG. 3 but showing the catheter in deflated condition.

DESCRIPTION OF THE PREFERRED EMBODIMENT

FIG. 3 illustrates a blood vessel 10 which is partially occluded by an extended occlusion 12. As shown, the vessel takes the form of an artery and the occlusion is what is commonly known as an arteriosclerotic plaque or atheroma. This is the type of adhering occlusion with which the subject catheter is expected to find primary application. It should be understood, however, that this catheter is useful in treating other types of occluded vessels where dilatation is desired. For example, the catheter may be used in treating occlusions resulting from fibromuscular displasia in veins.

The catheter 14 comprises a flexible plastic tube 16 having its proximal end attached to a manifold or syringe fitting 18 and having its distal end attached to an inflatable bag or balloon element 20, tip member 22 attached to the distal end of the balloon element 20, a flexible inner tube 24 having its distal end fixedly attached to tip member 22 and its proximal end fixedly attached to a handle or knob 26 having a threaded connection 28 with manifold 18, and a core wire 30 having a distal end 32 of square cross-section fitted within complementally shaped socket 34 of tip member 22 and having its proximal end fixedly attached to a knob 36 having a tapered end 38 extending into tapered bore 40 of handle or thumbscrew 26 and being thereby frictionally engaged with the thumbscrew for rotation therewith. A syringe 42 is removably attached to manifold 18.

It will be appreciated that tip member 22 is attached to thumbscrew 26 by flexible tube 24 and by core wire 30. The permanent connection between tube 24 and tip member 22 connects these two elements for rotative movement together and endwise movement together, while the separable connection between core wire 30 and tip member 22 serves to connect these two elements together for rotative movement only.

The catheter is used in the following manner. With the core wire 30 removed and with the balloon element 20 held in twisted, retracted condition by the thread connection between thumbscrew 26 and manifold 18, the catheter is inserted through an incision, not shown, into the artery and moved therealong until the balloon element 20 is disposed in alignment with the occlusion 12. The core wire 30 is then inserted so that its end 32 is engaged within the socket 34 of tip member 22 and so that the core wire knob 36 is frictionally engaged with thumbscrew 26. Thumbscrew 26 is then rotated in a clockwise direction to unwind balloon element 20. The syringe 42 is then attached to manifold 18 and pressurized fluid is introduced into balloon element 20 along the annular passageway between tubes 16 and 24 to inflate the balloon element and radially compress occlusion 12. After occlusion 12 has been compressed to the desired degree, the pressurized fluid is withdrawn from the balloon element and the syringe is removed from fitting 18. With the core wire 30 in place, as described, the thumbscrew 26 is rotated in a counterclockwise direction to twistingly collapse and retract balloon element 20. After the balloon element has been twisted to the degree desired, the core wire 30 is removed. The catheter is then in condition to be withdrawn from the artery or to be moved along the artery to another stenotic region.

The combination of the core wire 30 and the flexible inner tube 24 provides the degree of rigidity or strength necessary to provide the relatively large initial torque which is required to start twist-retraction of balloon element 20. However, the rigidity or strength required in a core element to provide the needed degree of initial torque makes the balloon section of the catheter too stiff for optimal movement of the catheter along a blood vessel. The wire 30 is made removable in this catheter so that the combined rigidity of the twisted balloon element and flexible tube 24 approximates the rigidity-flexibility characteristics of the balance of the catheter. Once the balloon element has been fully wound up and core wire 30 has been removed, the flexible tube 24 furnishes the lower value of torque which is required to keep the balloon element 20 in a wound-up condition.

What is claimed is:

1. A dilatation catheter comprising an elongated flexible tubular body member, a tip member in spaced relation to the distal end of the body member, an annular inflatable bag interconnecting the tip member and the distal end of the body member, and means extending through the body member and bag and attached to the tip member for axially rotating the tip member and thereby axially twisting the bag, said means comprising a flexible tubular member having a fixed connection with the tip member and a flexible rod-like member within said tubular member attached to the tip member for selective connection and disconnection with respect thereto.

2. The catheter of claim 1, said rod-like member comprising a wire provided at its distal end with a non-round cross-section having a slip-fit connection with a complementally shaped socket in the tip member.

3. The catheter of claim 2, said flexible tubular member being also adapted to guide the distal end of the wire to the socket of the tip member.

4. The catheter of claim 2, said tubular body member having its proximal end connected to a manifold for pressurized fluid, said flexible tubular member extending through said manifold and having its proximal end attached to knob means having a threaded connection with said manifold.

5. The catheter of claim 4, said wire having its proximal end attached to second knob means having a separable connection with said first-mentioned knob means.

6. A dilatation catheter comprising an elongated flexible tubular body member, a tip member in spaced relation to the distal end of the body member, an annular inflatable bag interconnecting the tip member and the distal end of the body member, and means comprising a selectively removable first element and a non-removable second element extending through the body member and bag and attached to the tip member for axially rotating the tip member and thereby axially twisting the bag.

7. The catheter of claim 6, said first and second elements together having a sufficient resistance to twist-shearing to initiate the axial twisting of the bag, the flexibility of the bag in twisted condition and said second element extending therethrough being substantially the same as the flexibility of the balance of the catheter.

* * * * *